United States Patent [19]

Hertel et al.

[11] 4,330,480

[45] May 18, 1982

[54] PREPARATION OF AMINOALKYL HALF-ESTERS OF SULFURIC ACID

[75] Inventors: Otto Hertel, Ludwigshafen; Karl-Heinz Beyer, Frankenthal; Albrecht H. Wallis, Ludwigshafen; Klaus Wulz, Ludwigshafen; Kamuran Izi, Ludwigshafen, all of Fed. Rep. of Germany

[73] Assignee: BASF Aktiengesellschaft, Fed. Rep. of Germany

[21] Appl. No.: 231,322

[22] Filed: Feb. 4, 1981

Related U.S. Application Data

[63] Continuation of Ser. No. 73,643, Sep. 10, 1979, abandoned.

[30] Foreign Application Priority Data

Sep. 18, 1978 [DE] Fed. Rep. of Germany ....... 2840554

[51] Int. Cl.$^3$ .......................................... C07C 141/02
[52] U.S. Cl. ................................................ 260/458 R
[58] Field of Search ................................... 260/458 R

[56] References Cited

U.S. PATENT DOCUMENTS 3,133,950  5/1968  Pizzarello et al. .............. 260/458 R
3,398,183  8/1968  Kindler et al. .................. 260/458 R

FOREIGN PATENT DOCUMENTS 1111854  5/1968  United Kingdom ........... 260/458 R

*Primary Examiner*—Nicky Chan
*Attorney, Agent, or Firm*—Keil & Witherspoon

[57] ABSTRACT

A process for the preparation of an aminoalkyl half-ester of sulfuric acid by simultaneously adding an aminoalkanol and sulfuric acid to a suspending medium, boiling at 70°–150° C., with vigorous mixing, distilling off the water formed during the reaction, and any water introduced with the starting materials, together with a part of the suspending medium, as an azeotrope, separating off the water from the condensed azeotrope and recycling the suspending medium, as a gas, to the reaction mixture.

7 Claims, No Drawings

PREPARATION OF AMINOALKYL HALF-ESTERS OF SULFURIC ACID

This is a continuation of application Ser. No. 73,643 filed Sept. 10, 1979, now abandoned.

The present invention relates to a process for the preparation of aminoalkyl half-esters of sulfuric acid by simultaneously adding an aminoalkanol and sulfuric acid to a suspending medium, boiling at 70°–150° C., with vigorous mixing, distilling off the water formed during the reaction, and any water introduced with the starting materials, together with a part of the suspending medium, as an azeotrope, separating off the water from the condensed azeotrope and recycling the suspending medium to the reaction mixture.

This process for the preparation of aminoalkyl halfesters of sulfuric acid is disclosed in German Pat. No. 1,241,458. In the process, the neutralization and the esterification are carried out simultaneously, and the heat of reaction is utilized for removing water by distillation. The suspending medium distilled off with the water is recycled, in the liquid state, to the reaction mixture, after having condensed the material which distils and having separated off the water.

It is an object of the present invention to increase the space-time yield of the process described above.

We have found that this object is achieved, according to the invention, by introducing fresh suspending medium as a gas into the reaction mixture, in order to replace the suspending medium which has been distilled off. Preferably, the gaseous suspending medium is superheated before being recycled to the boiling reaction mixture.

Examples of suitable aminoalcohols are ethanolamine, isopropanolamine, N-isopropylethanolamine, N-cyclooctylethanolamine, N-cyclooctylisopropanolamine, N-cyclohexylethanolamine and 3-aminopropanol. The preferred aminoalkanol used is ethanolamine. Of course it is also possible to employ mixtures of aminoalcohols for the esterification.

The concentration of the sulfuric acid is as a rule from 90 to 99% by weight. Either technical-grade or pure sulfuric acid can be used, as can sulfuric acid containing excess sulfur trioxide (fuming sulfuric acid).

Suitable water-immiscible suspending media are, advantageously, organic liquids which are stable to sulfuric acid, especially saturated hydrocarbons or mixtures of hydrocarbons which boil at from 70° to 150° C., especially from 100° to 130° C., under the pressure employed for the reaction. At lower boiling points, the rate of esterification becomes very low and furthermore very large amounts of dispersing medium must be distilled in order to remove the water, formed in the reaction, from the reaction mixture. Particularly suitable suspending media are technical-grade paraffin hydrocarbon mixtures which under atmospheric pressure start to boil at 100°–130° C., for example mixtures having a high octane content. The preferred suspending media are n-octane, iso-octane, and mixtures of the isomeric octanes. However, cyclic hydrocarbons, eg. cyclohexane, methylcyclohexane and cyclooctane, and halogen-substituted hydrocarbons, eg. carbon tetrachloride or perchloroethylene, or mixtures of the solvents mentioned, may also be used. As a rule, the neutralization and esterification of the aminoalkanols with sulfuric acid is carried out under atmospheric pressure, but it can also take place under reduced or superatmospheric pressure.

The reaction may be carried out, for example, by running the aminoalcohol and sulfuric acid, preferably in about equimolar amounts, slowly into the suspending medium, with vigorous mixing. However, it is also possible to use, for example, an excess of up to 10%, or even more, of one or other reactant. Advantageously, the ratio of aminoalkanol to sulfuric acid is kept constant during the reaction, but it is also possible to introduce a certain proportion of one component into the reactor initially. For example, it is possible first to introduce part of the aminoalkanol and only then to add the remaining aminoalkanol, simultaneously with the sulfuric acid. By using this method, the reaction mixture remains weakly alkaline, so that corrosion is avoided. The individual components are added to the reaction mixture at a rate such that the syrupy salt which first forms reacts further, to give the crystalline ester, before substantial amounts of the salt can accumulate in the suspension and form coarse agglomerates. For example, from 0.1 to 10 moles, preferably from 0.5 to 5 moles, of aminoalkanol, and a corresponding amount of sulfuric acid, are added per hour per liter of suspending medium.

If the preparation is carried out batchwise, it is advantageous if the starting materials are initially added particularly slowly. As soon as some of the crystalline ester has formed, the rate of addition can be increased. However, a high rate of addition of the starting materials can be used from the start if from 10 to 200 g, per liter of suspending medium, of previously crystallized aminoalkanol half-ester of sulfuric acid is added. This measure has proved particularly advantageous in the batchwise preparation of the aminoalkyl half-ester of sulfuric acid.

The water formed on neutralization and on esterification is distilled off, simultaneously with a part of the suspending medium, as an azeotrope. Preferably, the process is carried out continuously by condensing the azeotropic mixture, separating off the water from the condensate, vaporizing the suspending medium and recycling the resulting vapor into the boiling reaction mixture.

Whether the process is carried out continuously or batchwise, the temperature of the vaporized suspending medium can vary within a wide temperature range. It is at least as high as the boiling point of the suspending medium, and lies in the range from 110° to 200° C., preferably from 130° to 160° C. The suspending medium distilled, together with the water, from the reaction mixture is replaced and this is done, according to the invention, by introducing gaseous suspending medium into the reaction mixture. The suspending medium thus introduced can be either recycled suspending medium or freshly employed suspending medium or a mixture of both.

In preparing relatively small amounts of an aminoalkyl half-ester of sulfuric acid, a batchwise method of preparation is preferred, in which the water formed in the reaction is removed by means of the suspending medium as the entraining agent, and suspending medium vapor obtained by vaporizing fresh suspending medium is blown into the reaction mixture. The fresh suspending medium is introduced into the reaction mixture at about the same rate at which suspending medium is distilled from the reaction mixture.

The process according to the invention is particularly suitable for the continuous industrial preparation of an aminoalkyl half-ester of sulfuric acid. In that case, the suspending medium is preferably introduced into the reaction chamber at several inlet points at the bottom of the reaction vessel. Since the suspending medium is introduced as a gas, this method at the same time ensures stirring-up of the reaction mixture and hence better and less troublesome discharge of the half-ester product, which is obtained in crystalline form. Furthermore, it proves possible to remove the water, formed during esterification and neutralization, more rapidly than in the conventional process, where the suspending medium is introduced as a liquid into the reaction zone.

However, in all cases it is essential that the suspending medium introduced into the reaction vessel in order to replace the removed suspending medium should be in the form of a gas. This may be obtained by vaporizing condensed or freshly introduced suspending medium. The process is preferably carried out continuously, the condensed suspending medium being recycled as a gas. By this means, a higher space-time yield is achieved. The aminoalkyl half-ester of sulfuric acid, prepared by this process, has a more advantageous particle size, and is therefore more free-flowing and also drier, than a product obtained by the prior art process. A further advantage is that the new process is less prone to cause blockages and caking when discharging the reaction product.

The Examples which follow illustrate the invention.

EXAMPLE 12 moles of the β-aminoethyl half-ester of sulfuric acid and 2,000 ml of a mixture of n-octane and iso-octane are stirred, whilst boiling vigorously, in a stirred vessel equipped with an overflow nozzle and reflux condenser plus water separator. Per hour, 4 moles of concentrated sulfuric acid and 4 moles of monoethanolamine are introduced at a uniform rate. 660 ml, calculated as liquid, per hour of vaporized octane which has been superheated to 135°–140° C. are introduced into the stirred vessel from below, at several points. The octane is vaporized by means of a preheater and vaporizer.

The water formed in the reaction is distilled off continuously as an azeotrope with the suspending medium, and is then separated off. The octane mixture which has been distilled from the stirred vessel is continuously replaced by introducing a superheated gaseous octane mixture at 140° C.

The suspension of aminoethyl half-ester of sulfuric acid and octane runs continuously into a second reaction vessel of a cascade. In the first reaction vessel, about 90% of the water of reaction which has formed are expelled. On discharging the ester from the second, similar reaction vessel, the reaction is found to be virtually quantitative.

We claim:

1. A process for the preparation of an aminoalkyl half-ester of sulfuric acid, comprising;
    simultaneously adding an aminoalkanol and sulfuric acid to a suspending medium, boiling at 70°–150° C., with vigorous mixing,
    distilling off the water formed during the reaction, and any water introduced with the starting materials, together with a part of the suspending medium, as an azeotrope,
    separating off the water from the condensed azeotrope,
    vaporizing the suspending medium and recycling the gaseous suspending medium to the reaction mixture, and introducing fresh suspending medium, as a gas, into the reaction mixture in order to compensate for the suspending medium which has been distilled off.

2. A process as set forth in claim 1, wherein the recycled gaseous suspending medium is superheated before introduction into the reaction mixture.

3. A process as claimed in claim 1, wherein the temperature of the recycled gaseous suspending medium is from 110° to 200° C.

4. A process as set forth in claim 1, wherein said aminoalkanol is ethanolamine.

5. A process as set forth in claim 1, wherein the ratio of aminoalkanol to sulfuric acid is kept constant during the reaction.

6. A process as set forth in claim 1, wherein the temperature of the recycled gaseous suspending medium is from 130° to 160° C.

7. A process as set forth in claim 1, wherein said gaseous suspending medium is introduced into the reaction chamber at several inlet points at the bottom of the reaction vessel.

* * * * *